United States Patent
McIntyre

(10) Patent No.: US 8,332,044 B2
(45) Date of Patent: *Dec. 11, 2012

(54) PERCUTANEOUS ACCESS FOR NEUROMODULATION PROCEDURES

(75) Inventor: Jon T McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 357 days.

This patent is subject to a terminal disclaimer.

(21) Appl. No.: 12/194,002

(22) Filed: Aug. 19, 2008

(65) Prior Publication Data

US 2009/0030479 A1    Jan. 29, 2009

Related U.S. Application Data

(62) Division of application No. 11/178,540, filed on Jul. 11, 2005, now Pat. No. 7,415,309.

(51) Int. Cl.
- *A61N 1/32* (2006.01)
- *A61N 1/00* (2006.01)
- *A61N 1/34* (2006.01)

(52) U.S. Cl. .......................................... 607/116; 607/2

(58) Field of Classification Search .................... None
See application file for complete search history.

(56) References Cited

U.S. PATENT DOCUMENTS

| | | | |
|---|---|---|---|
| 3,995,644 A * | 12/1976 | Parsons | 607/116 |
| 5,464,446 A * | 11/1995 | Dreessen et al. | 607/116 |
| 7,937,160 B2 * | 5/2011 | Garabedian et al. | 607/116 |
| 2005/0182464 A1 * | 8/2005 | Schulte et al. | 607/115 |
| 2006/0129203 A1 * | 6/2006 | Garabedian et al. | 607/45 |

* cited by examiner

*Primary Examiner* — Carl H. Layno
*Assistant Examiner* — Jon-Eric C. Morales
(74) *Attorney, Agent, or Firm* — Fay Kaplun & Marcin, LLP

(57) ABSTRACT

A neuromodulation system, comprises an implantable electrode which is implanted within a body adjacent to a target nerve structure to which electric energy is to be applied via the electrode and a connection port which is implanted in the body with a proximal surface thereof substantially flush with an outer surface of a skin of the body, the connection port including a device interface for electrically connecting to an external device which remains external to the body in combination with an electric line extending from the device interface to the electrode for carrying electric energy from the external device to the electrode and a cover selectively closing an opening of the external surface of the implanted connection port.

18 Claims, 1 Drawing Sheet

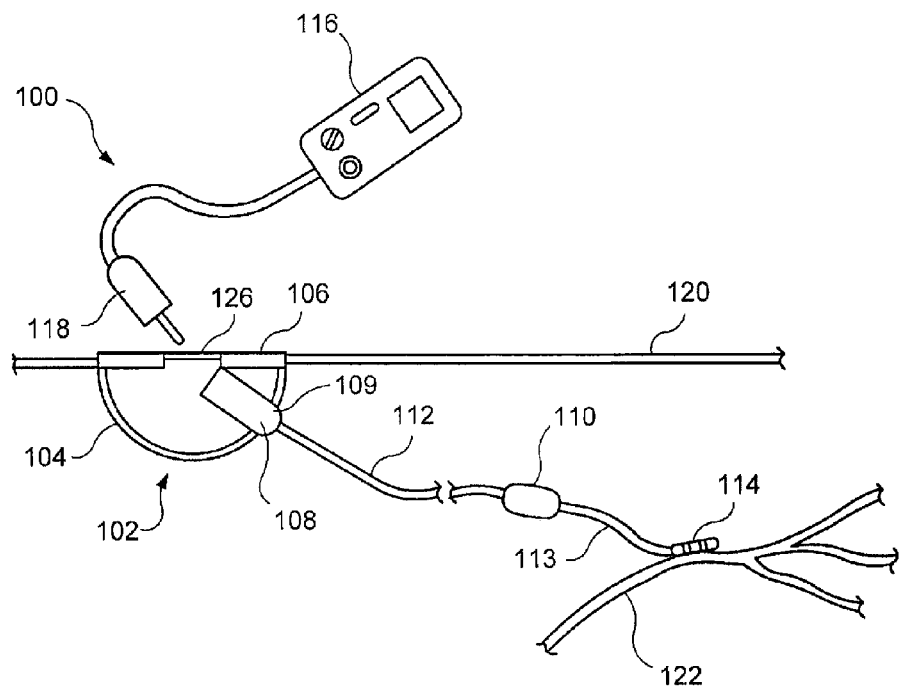
FIG. 1
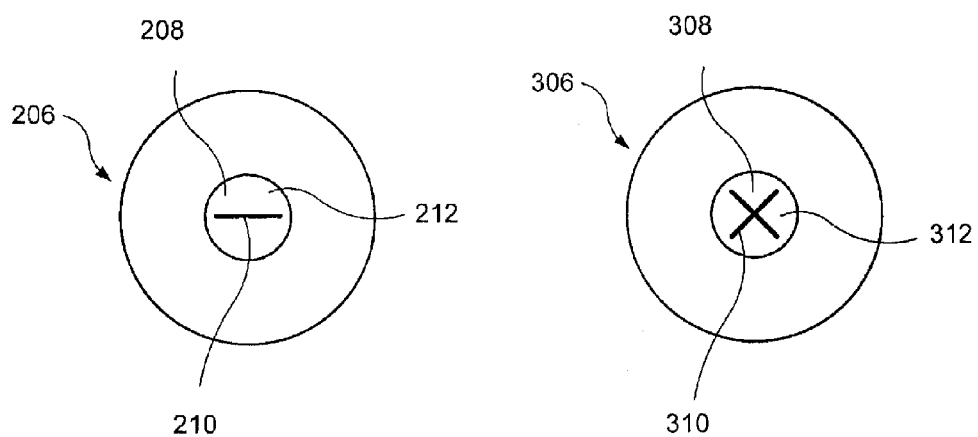
FIG. 2
FIG. 3

PERCUTANEOUS ACCESS FOR NEUROMODULATION PROCEDURES

PRIORITY CLAIM

This application is a Divisional application of U.S. patent application Ser. No. 11/178,540 filed on Jul. 11, 2005 now U.S. Pat. No. 7,415,309 entitled "Percutaneous Access for Neuromodulation Procedures". The entire disclosure of the prior application is considered as being part of the disclosure of the accompanying application and hereby expressly incorporated by reference herein.

BACKGROUND INFORMATION

Many debilitating medical conditions may be alleviated by stimulating targeted nerves and muscles. For example, electric current may be applied to a nerve or bundle of nerves to disrupt signals carried by, or to affect muscles controlled by, those nerves. Common examples of neural stimulation devices include cardiac pacemakers, devices to control epilepsy and chronic pain, etc.

In conventional applications, the ability of neuromodulation systems to operate over extended periods of time is limited by the endurance of their power supplies (e.g., batteries). This approach works well for devices used for short time periods, but can be problematic for devices which must operate beyond the life span of the batteries. For such devices, additional surgery may be necessary to replace the worn batteries. Alternatively, an external power supply carried by the patient may be connected to the implanted device by wires or other connections to provide a long lasting, constant power supply. However, the wires penetrating the skin increase the likelihood of infection and other negative reactions at the location where the connections penetrate the skin.

The size of components of conventional implanted neuromodulation systems often causes discomfort and may reduce a patient's ability to carry out routine tasks. In addition, the cost of such implanted devices (e.g., implanted pulse generators) may be significant. Implanted pulse generators also have a limited life span, usually around 5 to 10 years, after which they must be replaced. As with batteries, this may involve additional surgery with the associated discomfort and costs. It may also be extremely difficult to perform upgrades or repairs to conventional, implanted pulse generators due to the same concerns described above.

SUMMARY OF THE INVENTION

In one aspect, the present invention is directed to a neuromodulation system, comprising an implantable electrode which is implanted within a body adjacent to a target nerve structure to which electric energy is to be applied via the electrode and a connection port which is implanted in the body with a proximal surface thereof substantially flush with an outer surface of a skin of the body, the connection port including a device interface for electrically connecting to an external device which remains external to the body in combination with an electric line extending from the device interface to the electrode for carrying electric energy from the external device to the electrode and a cover selectively closing an opening of the external surface of the implanted connection port.

In a further aspect, the present invention is directed to a method for neuromodulation therapy, comprising surgically implanting an electrode adjacent to a target nerve structure and implanting a connection port including a housing which, when implanted, lies beneath a surface of the skin, the housing defining an opening to a surgically created opening in the skin, the connection port including a device interface for electrically coupling to an external device and a cover selectively sealing the opening in combination with forming a tunnel between the incision site and the implanted connection port and passing an electric line though the tunnel to connect the device interface and the electrode. A connector of an external medical device is inserted through the opening and coupled to the device interface electric current is applied from the external device to the electrode via the device interface and the electric line.

BRIEF DESCRIPTION OF DRAWINGS

FIG. 1 shows a diagram of a neuromodulation system with external pulse generator according to an embodiment of the present invention;

FIG. 2 shows a diagram of a passive valve used in a connector for a neuromodulation system according to the present invention; and FIG. 3 shows a diagram of another passive valve used in a connector for a neuromodulation system according to the present invention.

DETAILED DESCRIPTION

The present invention may be further understood with reference to the following description and the appended drawings, wherein like elements are referred to with the same reference numerals. The present invention relates to devices used to block nerve signals and to stimulate selected nerves. In particular, the present invention relates to nerve stimulation devices comprising a first implanted portion and a second external portion connected to the implanted portion through an implanted connection port.

As described above, a variety of medical disorders are now treated via neuromodulation (i.e., the application of electrical stimuli to a targeted nerve or bundle of nerves). The stimulation may be designed to interfere with the electrical activity of the target nerves by blocking it, or by applying different electrical signals to the nerve(s). As would be understood by those skilled in the art, such procedures may be employed to treat a variety of ailments including, for example, movement disorders such as Parkinson's disease and Multiple Sclerosis, epilepsy, chronic pain, stroke, Alzheimer's disease, head injuries, spinal chord injuries, Hydrocephalus, obesity, urinary urge incontinence, fecal incontinence, interstitial cystitis, chronic pelvic pain and psychological disorders such as depression. Depending on the condition being treated, different stimuli may be applied to the target nerve(s). However, in general, the hardware components used are substantially similar.

The treatment of urinary urge incontinence, for example, often involves the implantation of a bulky and expensive Pulse Generator (IPG). The IPG generates electrical pulses the intensity and duration of which are tailored to supply desired signals to the nerves connected to specific muscles. IPG's have a finite life of about 5 to 10 years after which they must be replaced through invasive surgery. One example of an IPG for treating urinary urge incontinence is the Interstim device, available from the Medtronic Corporation.

To reduce the costs of neuromodulation treatment, a system according to the present invention utilizes external components in place of several of the implanted components of prior systems. This approach reduces patient discomfort and eliminates additional surgery for replacing or updating most of the system components. In these systems, a lead and electrodes are implanted with the electrodes in contact with, or in proximity to, the target nerve(s). A connection port is implanted at a convenient location (e.g., in proximity to the lead or a selected distance therefrom with an extension connecting the lead to the implanted connection port). The bulkier and more expensive components of these systems (e.g., the pulse generator) remain external and are connected to the implanted components via the implanted connection port.

The embodiments of the present invention describe a neuromodulation system utilizing an implanted connection port to facilitate neuromodulation and/or neurostimulation procedures, eliminating the need for an IPG (or other large device) by allowing connection between the electrodes and external devices via the implanted port. The port may be placed substantially even with a level of the skin and may include a housing which extends a small distance below the skin level. The port is connected to a lead with electrodes which interface with a targeted nerve structure (e.g., a nerve, nerve bundle or nerve junction) to allow external devices to be connected to the electrode leads for the application of various therapeutic signals (e.g., test stimulation signals and/or predetermined neuromodulation signals) to the target nerve structure. The external devices which can be connected to the implanted connection port include, but are not limited to, Test Stimulators, Programmers and Pulse Generators. These devices may be hand held, table top mounted, or may be wearable by the patient to enhance patient mobility.

Using a connection port at the skin level to couple one or more external components (e.g., a pulse generator) to electrodes greatly reduces the cost of the implant. Both the implantation and subsequent care and maintenance of the system are simplified decreasing discomfort and reducing the risks and costs associated with surgery. The system also increases flexibility in selecting treatment options, and frees the patient to select between a larger number of physical locations at which the treatment may be performed. The connection port according to the invention allows the connection of a table top pulse generator located, for example, at a physician's office, a hospital, or in the patient's home. Hand held devices or other portable devices may then be employed at any time and/or place desired by the patient or physician. In addition, a patient wearable external device may be placed on a belt, a wristband or carried in a pocket.

FIG. 1 shows an exemplary embodiment of a neuromodulation system 100 according to the invention, which includes an implantable connection port 102. The system 100 is designed to stimulate a target nerve structure 122 with electrical impulses. According to embodiments of the invention, the implanted connection port 102 is used to connect one or more external components of the system 100, for example a pulse generator or programmer 116, to an implanted extension 112 coupled to a lead 113 extending to electrodes 114 which are coupled to a distal end thereof. In many cases, the electrodes 114 will be positioned adjacent to the target nerve structure 122 with the lead 113 extending therefrom to a proximal end connected to the implanted connection port 102 either directly or via the extension 112. In many cases, the distance between the implanted connection port 102 and the electrodes 114 will be minimized. However, when longer distances are necessary to simplify the surgical procedure and/or to enhance patient comfort, an extension 112 with an extension connector 110 may be coupled to the proximal end of the lead 113 to span the distance between the implanted connection port 102 and the target nerve structure 122, as shown in FIG. 1.

According to the exemplary embodiment shown in FIG. 1, the implanted connection port 102 comprises a housing 104 that is placed below the skin layer 120. A connection jack 108 is mounted within the housing 104 connected to the extension cable 112 that extends out of the housing 104 to the extension connector 110 which is connected to the lead 113 and the electrodes 114. The lead 113, the electrodes 114, the extension cable 112 and the connector 110 are positioned by tunneling to the electrode implant site and feeding the electrodes 114, the lead 113, the connector 110 and the extension cable 112 through the surgical tunnel until the electrodes 114 reach the electrode implant site while the proximal end of the extension cable 112 extends to the connection jack 108 in the implanted connection port 102. Those skilled in the art will understand that the extension cable 112 may be provided in different lengths to accommodate different distances between the site of the port 102 and the electrode implant site and that the extension cable may be connected directly to the lead 113 without the extension connector 110. During assembly of the implanted connection port 102, the extension cable 112 may be passed through an opening 109 of the housing 104, and connected to the connection jack 108 which may then be sealingly fixed to the housing 104. FIG. 1 shows one pair of electrodes. it is understood that multiple pairs can be employed to increase the likelihood of stimulating the correct site, or to selectively activate electrodes to maximize treatment on an ongoing basis (for example if lead migration occurs).

According to the exemplary embodiment of the invention, the housing 104 of the implanted connection port 102 comprises a passive elastomeric valve 126 covering an external portion of the housing 104. More specifically, the housing 104 comprises a cover 106 which covers an entire outward facing opening of the housing 102. The cover 106 preferably includes the passive elastomeric valve 126 over a portion thereof. In one embodiment, the passive elastomeric valve 126 comprises a disk made from an elastomer, such as silicon, C-Flex, latex, etc., with one or more slits cut thereinto. These slits are biased to a closed position by the elastomeric material. However, as would be understood by those skilled in the art, these slits may be easily opened by pushing an electrical connector or other component therethrough to enter the housing 102 and connect to the connection jack 108. In another embodiment, the cover 106 may be a hinged cap. The cover 106 and the passive valve 126 prevent contaminants such as dirt, fluids, bacteria etc. from entering the housing 104. At the same time, the passive valve 126 facilitates insertion of an electrical lead, such as a connector 118 of a pulse generator 116, into the housing 104, so that it may be mated to the connection jack 108. The connection jack 108 may, for example, be a standard phone jack configured to receive an electrical connector such as a shrouded multi-conductor phone connector. However, those skilled in the art will understand that any of a variety of known or custom connection jacks may be used for the connection jack 108 so long as it is configured to receive the connector of the device(s) which are to be connected to the electrodes 114. Those skilled in the art will understand that the slits may take on any of a variety of shapes extending along portions of one or more curves, tricuspid shapes, etc.

FIG. 2 shows an exemplary embodiment of a cover 206 with a passive elastomeric valve 208, according to the invention. The valve 208 is formed of a thin (0.005"-0.100") elastomeric membrane 212 with a slit 210 cut therethrough. The dimensions of the membrane 212 and of the slit 210 may be adjusted to obtain the desired closing force which retains the valve normally closed, and may vary depending on the material forming the valve 208. FIG. 3 shows an alternative exemplary embodiment of a cover 306 according to the invention. Here, the cover 306 has a passive elastomeric valve 308 formed of a membrane 312 with a pair of slits 310 arranged in a cruciform pattern. The slits 310 preferably have a size and shape optimized for insertion of an electrical contact therethrough with a natural shape of the membrane 308 urging the and to retain the valve 308 closed in normal operation, when the electrical contact is removed.

In a different embodiment according to the invention, the cover 106, 206 and 306 of the housing 104 may be replaced by a simple removable cap. In this manner, the additional expense of manufacturing a passive valve is eliminated. For example, the removable cap may be removed to permit insertion of the connector 118 into the housing 104. When the connector 118 is not in use, the housing 104 is closed by replacing the cap. In a different exemplary embodiment, the connector 112 and the connector jack 108 are formed integrally with the housing 104. In this case, the implanted connection port 102 may preferably be provided with extension cables 112 of different lengths to suit a variety of applications. In addition, the extension cables 112 and other component of the system 100 may preferably be coated with an antimicrobial compound, to prevent infection.

During an exemplary procedure for implanting a neurostimulation system according to the present invention, an incision is made and the electrodes 114 are placed adjacent to the target nerve structure 122. A tunnel is then surgically formed between the site at which the electrodes 114 are implanted and the site at which the implanted connection port 102 is to be placed with the lead 113 extending into the tunnel toward the site of at which the connection port 102 is to be implanted. In some cases, these two locations are substantially the same, and tunneling is not necessary. A temporary sheath may be left behind in the tunnel site, so that the extension cable 112 can later be fed through the sheath to be joined to the proximal end of the lead 113. As would be understood by those skilled in the art, the extension cable 112 may be made available in different lengths to accommodate different tunneling distances. After the extension cable 112 has been positioned, the sheath is removed over the cable, and the extension cable 112 is mated to the lead 113 via the extension connector 110. The incision at the site of the implantation of the electrodes 114 may then be closed and the implanted connection port 102 is fixed to the skin using conventional methods as would be understood by those skilled in the art.

A test stimulation of the target nerve structure 122 may then be performed to verify the appropriate response prior to final implantation. After the surgical aspects of the procedure have been completed, the implanted connection port 102 is used to connect external components to the electrodes 114 via the lead 113. For example, the connector 118 of a pulse generator 116 may be inserted into the housing 104 through the passive elastomeric valve 126 and connected to the connection jack 108. As would be understood by those skilled in the art, various therapeutic stimuli may then be delivered directly to the target nerve structure 122 based on, for example, a schedule selected by medical personnel programmed into the pulse generator 116.

The present invention has been described with reference to specific exemplary embodiments. Those skilled in the art will understand that changes may be made in details, particularly in matters of shape, size, material and arrangement of parts. Accordingly, various modifications and changes may be made to the embodiments. For example, the location of the implanted components of the system may be varied to reflect the location of the nerves and muscles that are to be stimulated. Additional or fewer components may be located external to the body of the patient, depending on the condition that is being treated using the neurostimulation system. The specifications and drawings are, therefore, to be regarded in an illustrative rather than a restrictive sense.

What is claimed is:

1. An implantable connection port for coupling an external device to a surgically implanted electrode, comprising:
    a housing defining an interface chamber therewithin and a proximal opening which, when the housing is in an operative position, faces an outer surface of a skin of a body within which the connection port is implanted;
    a cover extending across an opening in the housing wherein, when in an operative position, the cover lies substantially flush with the outer surface of the skin with the housing extending beneath the cover within the body, the cover being selectively openable to receive an electrical connector of an external device through the opening in the housing; and
    a connection jack mounted within the housing for coupling to an electrical connector of the external device,
    wherein the cover includes a passive valve biased toward a closed position, the valve being openable to receive the electrical connector therethrough.

2. The connection port according to claim 1, wherein the passive valve includes a slitted elastomeric membrane.

3. The connection port according to claim 1, wherein the cover comprises a removable cap.

4. The connection port according to claim 1, wherein the cover comprises a hinged cap.

5. The connection port according to claim 1, further comprising an extension cable extending from the connection jack through a wall of the housing for connection to an implanted electrode.

6. The connection port according to claim 1, wherein the connection jack is integral with the housing.

7. The connection port according to claim 1, wherein the housing further comprises an antimicrobial agent coating.

8. The connection port according to claim 1, wherein the housing is adapted to be sutured to the skin.

9. The connection port according to claim 2, wherein the slitted elastomeric membrane is made of one of silicon, C-Flex and latex.

10. The connection port according to claim 2, wherein the slitted elastomeric membrane comprises one of a linear slit, a cross-shaped slit and a tricuspid slit.

11. The connection port according to claim 2, wherein the slitted elastomeric membrane comprises one of a linear and a cruciform slit.

12. An implanted connection port for an external medical device, comprising:
    a housing which, when in an operative position, is implanted under a skin of a body;
    an openable cover of the housing which, when in an operative position, is accessible from outside the body; and
    a connection jack within the housing, the jack including a proximal end connectable to a connector of an external device when the cover is open and a proximal end coupled to an electric line for connection to an implanted electrode,
    wherein the cover includes a passive valve biased toward a closed position, the vale being openable to receive the electrical line therethrough.

13. A method for performing a neuromodulation procedure, comprising:
    implanting in a body an electrode, wherein a distal end of the electrode is adjacent to a target nerve;

implanting a connection port adjacent to a skin of the body, wherein substantially all of the connection port is implanted beneath the skin;

connecting a proximal end of the electrode to a first opening of the connection port; and connecting a device to the proximal end of the electrode via a second opening of the connection port, the connection port including a cover extending across the second opening, wherein the device remains external to the body, wherein the device delivers electricity to the distal end of the electrode, and wherein the cover includes a passive valve biased toward a closed position, the valve being openable to receive an electrical connector of the device therethrough.

14. The method according to claim 13, wherein the device is a pulse generator.

15. The method according to claim 13, wherein the step of connecting the device to the proximal end of the electrode includes coupling a first connecting element joined to the proximal end of the electrode to a second connecting element joined to a wire that extends from the device.

16. The method according to claim 15, wherein the first connecting element is located at the first opening of the connector port, and the second connecting element is located at the second opening of the connector port.

17. The method according to claim 13, wherein when in an operative position, the cover lies substantially flush with the outer surface of the skin with a remainder of the connector port extending beneath the cover within the body.

18. The method according to claim 13, wherein the passive valve includes a slitted elastomeric membrane.

* * * * *